(12) United States Patent
Baruch et al.

(10) Patent No.: US 7,744,541 B2
(45) Date of Patent: Jun. 29, 2010

(54) CEREBRAL VASCULAR REACTIVITY MONITORING

(75) Inventors: Robert A. Baruch, Ellicott City, MD (US); Ken M. Brady, Owings Mills, MD (US)

(73) Assignees: Raba Equity Partners II, LLC, Ellicott City, MD (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/181,502

(22) Filed: Jul. 29, 2008

(65) Prior Publication Data

US 2010/0030054 A1    Feb. 4, 2010

(51) Int. Cl.
*A61B 5/00* (2006.01)
(52) U.S. Cl. .................. 600/483; 600/300; 600/504
(58) Field of Classification Search .............. None
See application file for complete search history.

(56) References Cited

U.S. PATENT DOCUMENTS

| | | | |
|---|---|---|---|
| 6,802,812 B1 | 10/2004 | Walker et al. | 600/309 |
| 7,532,919 B2* | 5/2009 | Soyemi et al. | 600/323 |
| 2004/0049105 A1 | 3/2004 | Crutchfield et al. | |
| 2006/0094964 A1 | 5/2006 | Ragauskas et al. | 600/454 |
| 2007/0287922 A1 | 12/2007 | Tanaka et al. | |
| 2008/0208011 A1* | 8/2008 | Shuler | 600/301 |
| 2009/0093703 A1* | 4/2009 | Silber | 600/410 |

FOREIGN PATENT DOCUMENTS

| | | |
|---|---|---|
| JP | 2002-177248 | 6/2002 |
| WO | WO 2008/097411 | 8/2008 |

OTHER PUBLICATIONS

L.A. Steiner et al., "Cerebrovascular Pressure Reactivity is Related to Global Cerebral Oxygen Metabolism After Head Injury", J. Neurology, Neurosurgery & Psychiatry, vol. 74, 2003, pp. 765-770.

C. Dean Kurth et al., "Cerebral Hemoglobin and Optical Pathlength Influence Near-Infrared Spectroscopy Measurement of Cerebral Oxygen Saturation", Anesthesia & Analgesia, vol. 84, 1997, pp. 1297-1305.

Ken M. Brady et al., "Continuous Time-Domain Analysis of Cerebrovascular Autoregulation Using Near-Infrared Spectroscopy", Stroke: Journal of the American Heart Association, vol. 38, Aug. 30, 2007, pp. 2818-2825.

(Continued)

*Primary Examiner*—Robert L Nasser
(74) *Attorney, Agent, or Firm*—Snyder, Clark, Lesch & Chung, LLP

(57) ABSTRACT

A monitoring device may include logic to receive arterial blood pressure data associated with a patient and receive tissue hemoglobin data associated with the patient. The logic may also calculate a linear correlation between the arterial blood pressure data and the tissue hemoglobin data. The correlation may be used to assess vascular reactivity.

21 Claims, 9 Drawing Sheets

OTHER PUBLICATIONS

NIRO-100 Near Infrared Oxygenation Monitor product guide, Jul. 2003, 2 pages.

NIRO-200 Near Infrared Oxygenation Monitor product guide, Aug. 2003, 2 pages.

Volume Clamp, Finapress Website, 2007, 1 page from http://www.finapress.com/customers/volume_clamp.php.

Finometer PRO & MIDI, Finapress Website, 2007, 2 pages from http://www.finapress.com.customers/finometer.php.

Fore-sight, Artemis Medical website, 2 pages from http://www.artemismedical.co.uk/casmedical_fore-sight.html.

INVOS Cerebral Oximeter Principles of Operation, Somanetics website, 2006, 3 pages from http://www.somanetics.com/invos_principles.htm.

The INVOS System, Somanetics website, 2006, 1 page from http://www.somanetics.com/invos.htm.

International Search Report and Written Opinion dated Mar. 24, 2010 issued in corresponding PCT application No. PCT/US2009/051364, 11 pages.

* cited by examiner

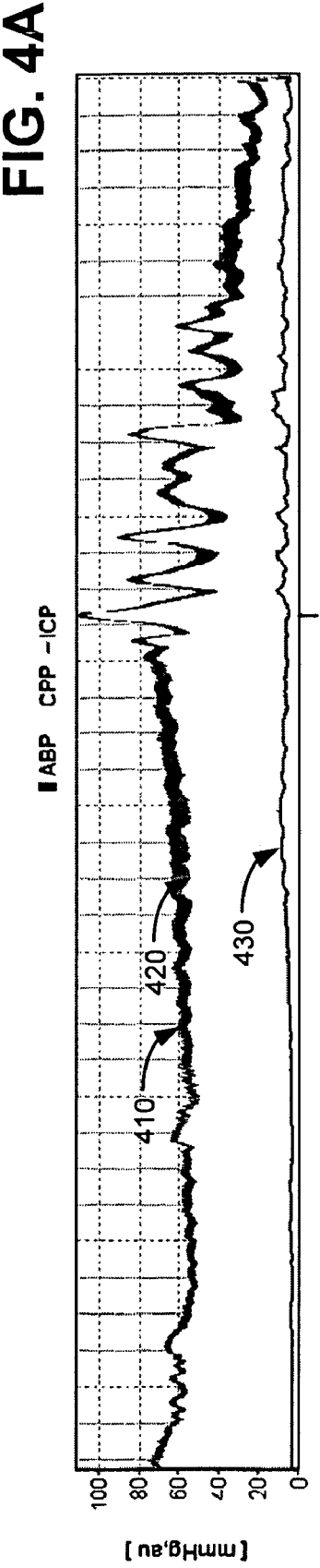
FIG. 4A
FIG. 4B
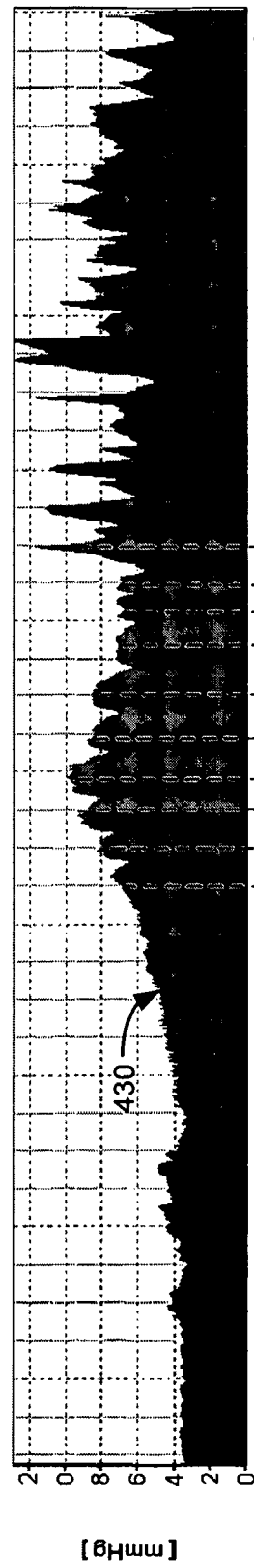
FIG. 4C

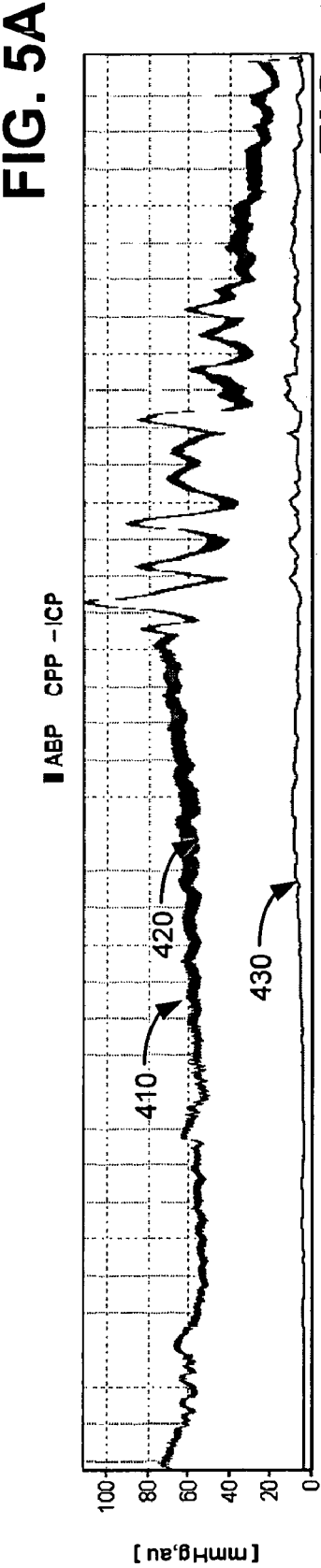
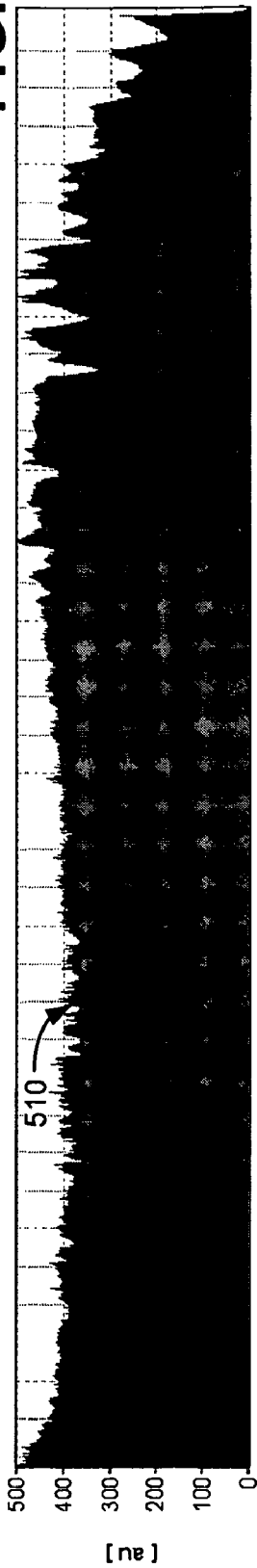
FIG. 5A
FIG. 5B
FIG. 5C

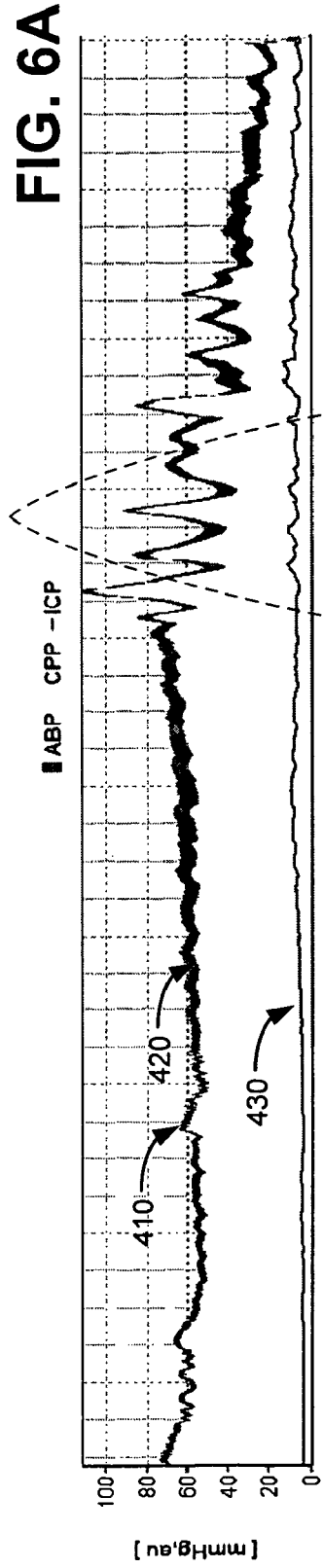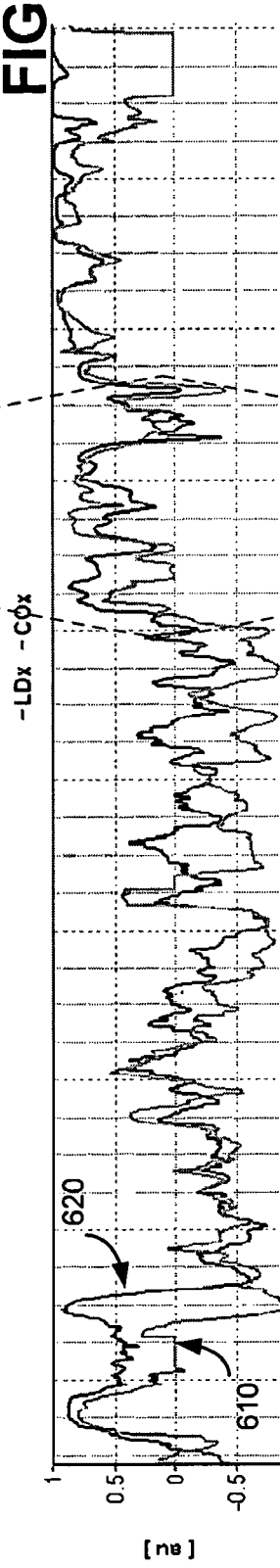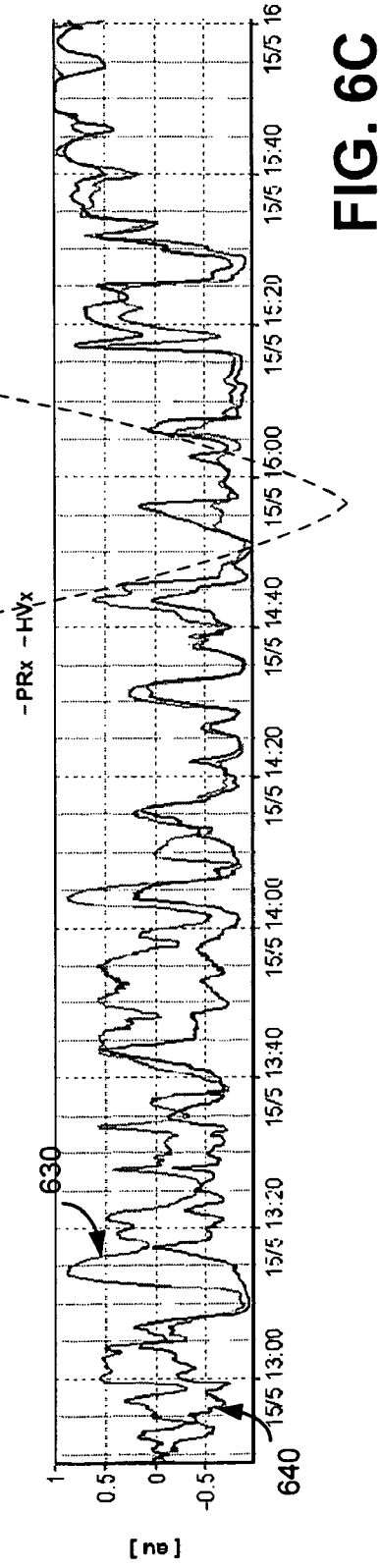

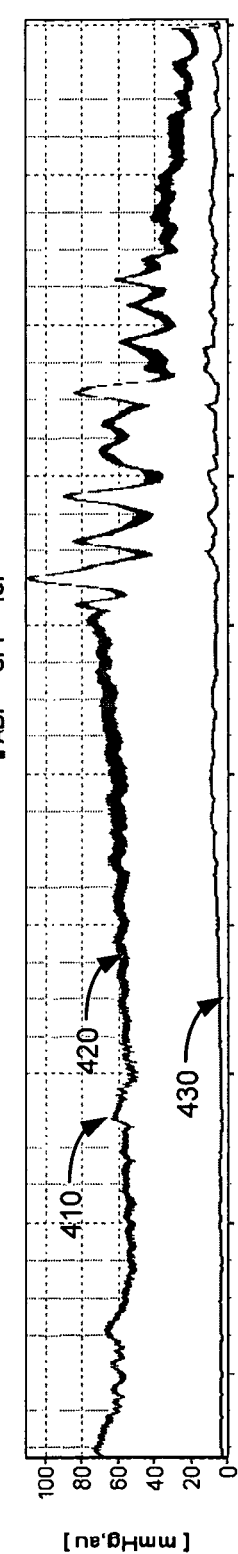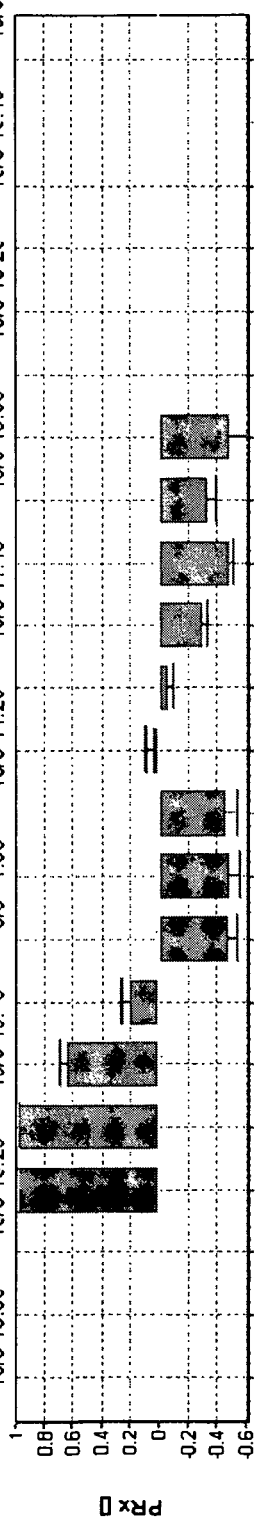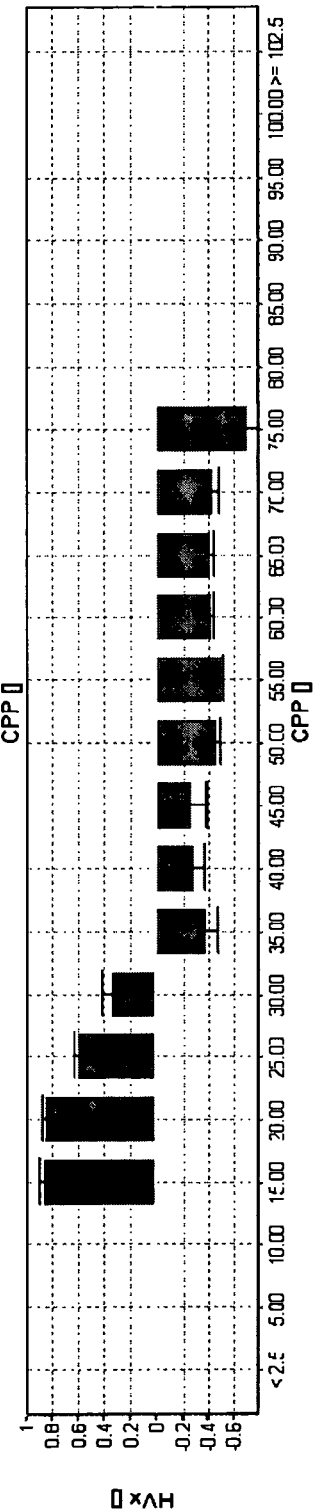

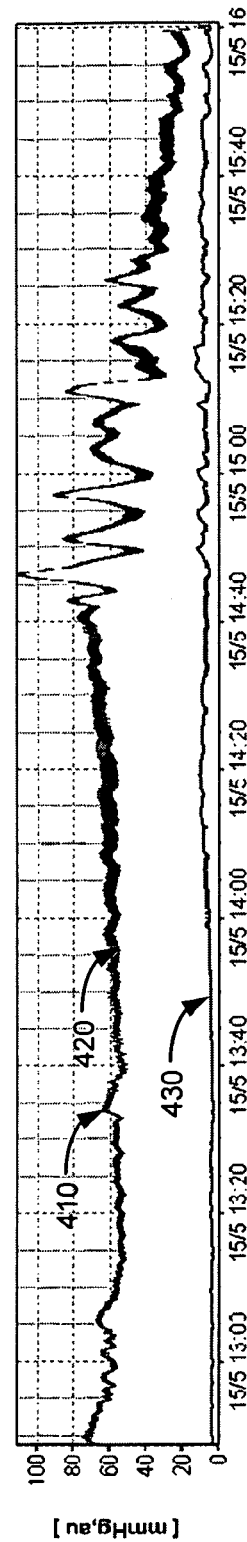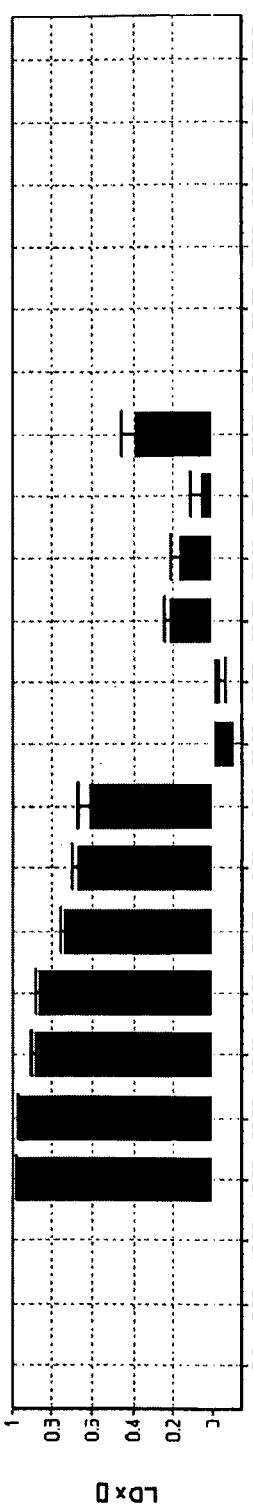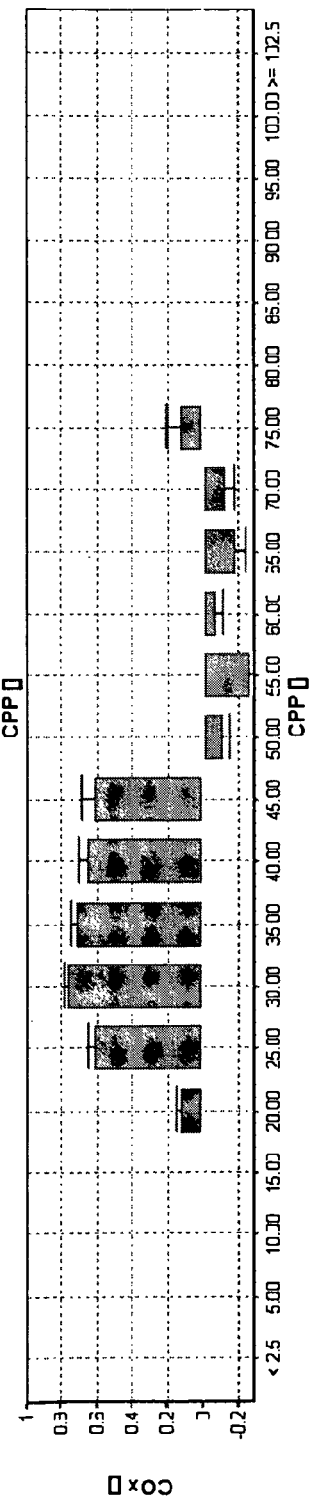

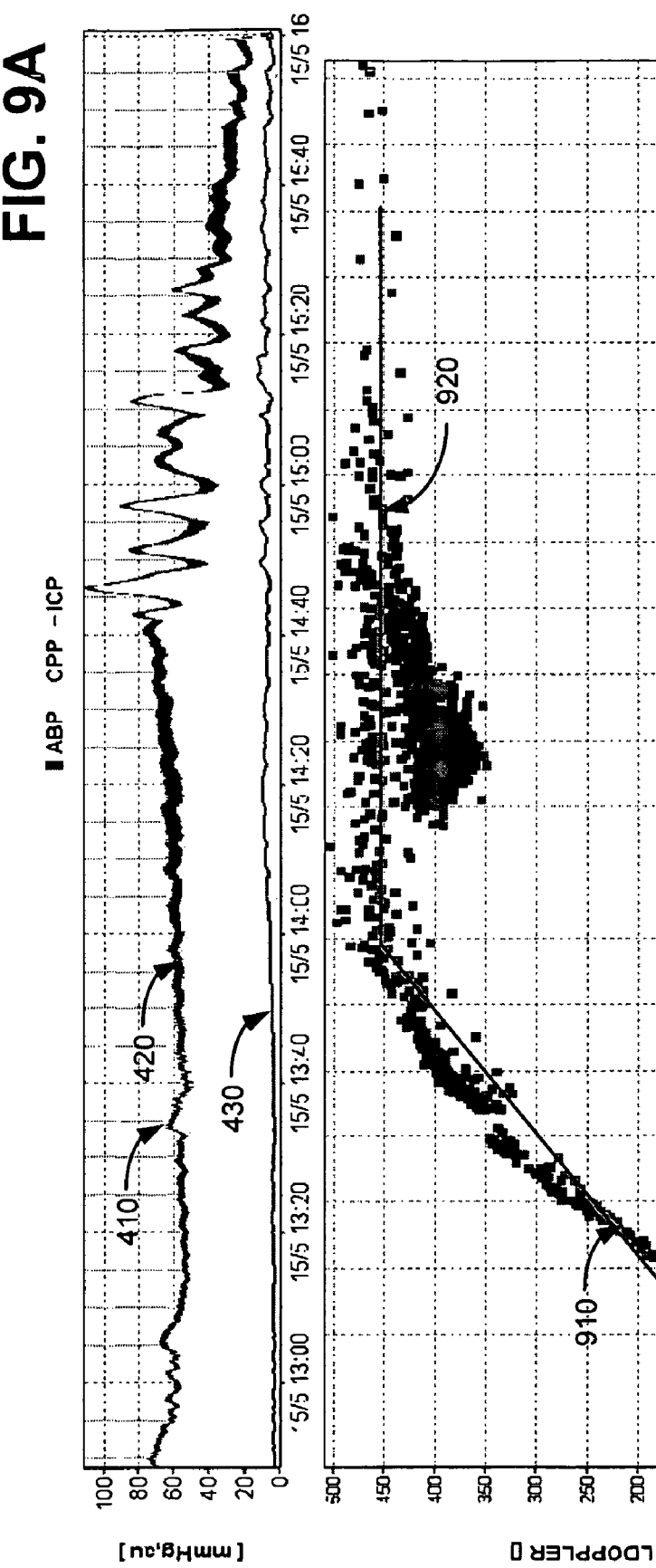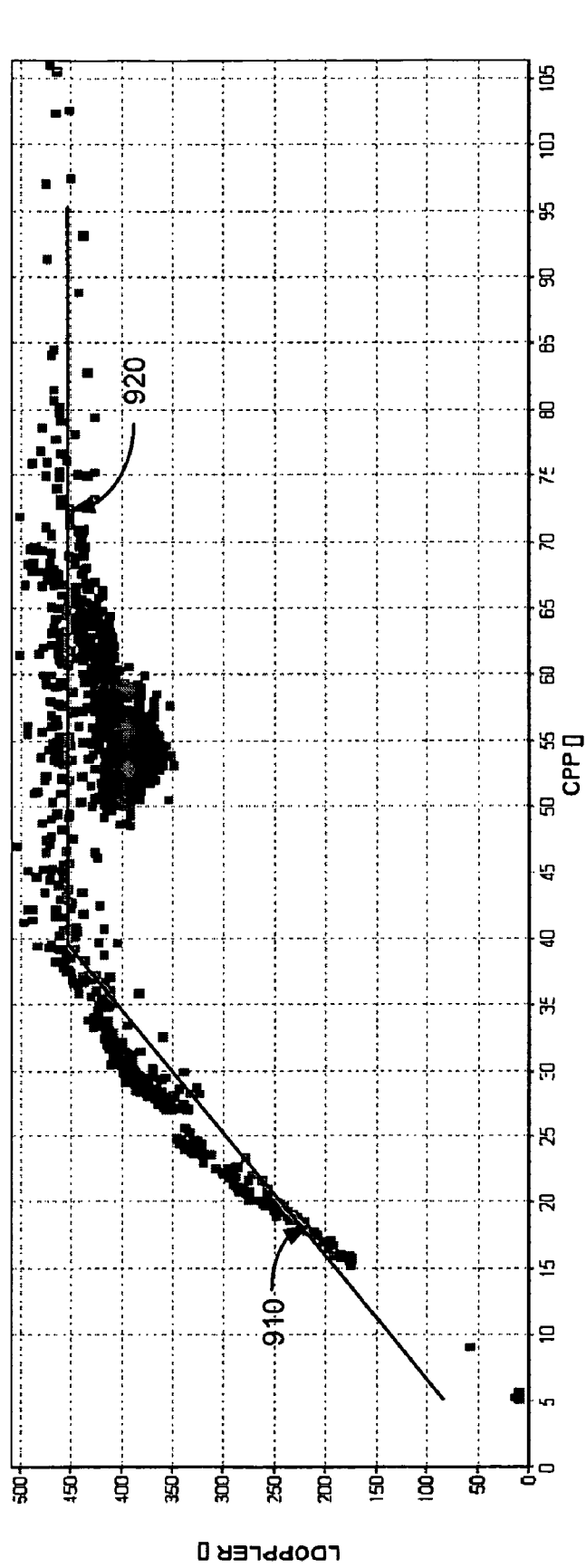

CEREBRAL VASCULAR REACTIVITY MONITORING

BACKGROUND INFORMATION

Cerebral pressure autoregulation is typically defined as the maintenance of a constant cerebral blood flow (CBF) in the face of changing cerebral perfusion pressure (CPP). In healthy individuals, this process protects the brain during transient changes in arterial blood pressure (ABP). However, various medical traumas, such as traumatic brain injuries, strokes, cardiopulmonary bypass, etc., may impair cerebral pressure autoregulation. Impairment of autoregulation narrows the range of blood pressures at which flow is matched to metabolic needs.

The brain's primary mechanism to maintain constant or nearly constant CBF is by varying the resistance associated with blood vessels supplying blood to the brain. For example, the brain may control the diameters of these blood vessels to allow the blood vessels to supply more or less blood to the brain, depending on the metabolic need. Therefore, vascular reactivity is an important component by which constant blood flow to the brain is maintained.

One current medical diagnostic method to measure or assess cerebral vascular reactivity generates a pressure reactivity index that uses intracranial pressure as a surrogate of intracranial blood volume, and detects passivity of blood volume to arterial blood pressure, which is used to indicate loss of vascular reactivity. Such methods, however, require complex monitoring devices, such as transcranial probes, that are cumbersome and difficult to maintain in the proper position on a patient to obtain accurate data, or intracranial probes that must be inserted into the skull of a patient. As a result, such methods may be ill-suited for use with many types of patients, such as patients in critical condition, pediatric patients, geriatric patients, etc.

BRIEF DESCRIPTION OF THE DRAWINGS

FIGS. 4A-9B illustrate experimental data associated with assessing cerebral vascular reactivity.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention. Instead, the scope of the invention is defined by the appended claims and their equivalents.

Implementations described herein provide for measuring hemoglobin, such as a relative total hemoglobin (rTHb) concentration, in an organ, such as the brain. When the hemoglobin (e.g., rTHb) in tissue, such as brain tissue, is measured in the manner described below, the hemoglobin concentration may be a function of blood volume in the tissue, as expanding or contracting blood volume increases or decreases the total hemoglobin density in the tissue. The rTHb may, therefore, act as a surrogate for cerebral blood volume and may be used to assess vascular reactivity of the organ. Implementations described herein may also continuously monitor the rTHb and generate a hemoglobin volume index that acts as a continuous assessment of cerebral vascular reactivity.

Figure 1:
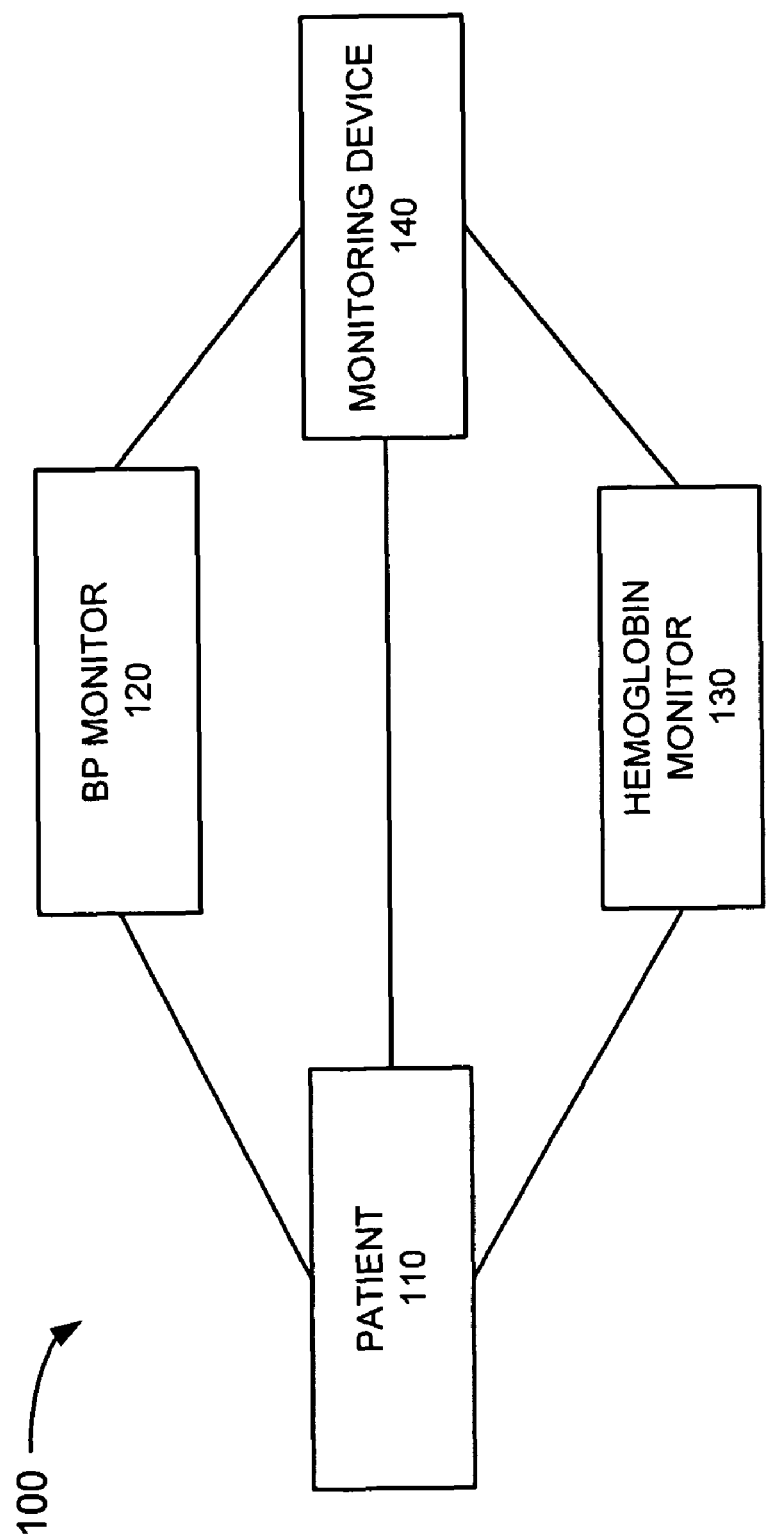
FIG. 1 illustrates an exemplary environment in which systems and methods described herein may be implemented.

FIG. 1 is a block diagram of an exemplary environment in which systems and methods described herein may be implemented. Referring to FIG. 1, environment 100 may include a patient 110, a blood pressure (BP) monitor 120, a hemoglobin monitor 130 and a monitoring device 140.

Patient 110 may represent any person (i.e., an adult or child) that may be in a state of medical distress or has sustained an injury. BP monitor 120 may be any type of BP monitoring device, such as a device that includes or is coupled to an invasive arterial line that includes a catheter or some other device used to measure arterial blood pressure (ABP) of patient 110. In an exemplary implementation in which a catheter is used to measure the ABP, the catheter may be an arterial catheter that is inserted in the wrist, foot or some other part of patient 110. The catheter may include a sensor to measure pressure in the artery and may also include a transducer to convert the measured pressure into electrical signals corresponding to the measured pressure. Alternatively, BP monitor 120 may include a non-invasive device, such as a device that uses a finger cuff (e.g., a device manufactured by Finapres Medical Systems) to monitor the ABP of patient 110.

Hemoglobin monitor 130 may include any monitoring device able to measure rTHb, or some measure of total or relative tissue hemoglobin, in an organ. For example, in one implementation, hemoglobin monitor 130 may include a continuous reflectance near infrared (IR) spectroscope used to measure total tissue hemoglobin in an organ, such as the brain. In this implementation, hemoglobin monitor 130 has a near IR source that emits radiation in the near IR range (e.g., from about 600 nanometers to about 2500 nanometers), which allows the radiation to penetrate through a target organ, such as the brain, and a detector that detects the reflected intensity of the received radiation at one or more wavelengths. Based on the absorption of a portion of the near IR radiation by the brain tissue, a total hemoglobin concentration, or density, in the brain may be obtained. Exemplary devices capable of performing this type of tissue hemoglobin concentration monitoring/measuring include the NIRO series of monitors manufactured by Hamamatsu, the INVOS series of monitors manufactured by Somanetics and the FORE-SIGHT monitor manufactured by CAS Medical Systems.

Monitoring device 140 may include a device used to continuously monitor various parameters associated with patient 110. In an exemplary implementation, monitoring device 140 may receive data from BP monitor 120 and/or hemoglobin monitor 130 and generate a hemoglobin volume index in a real-time or near real-time manner. The hemoglobin volume index may be used to continuously assess cerebral vascular reactivity. This information may then be used to assess autoregulation functioning of the brain. That is, the hemoglobin volume index may be used to assess whether the brain is able to regulate its blood flow and/or determine parameters, such as a blood pressure or CPP, at which the brain is unable to autoregulate properly, as described in detail below.

Exemplary environment 100 illustrated in FIG. 1 is provided for simplicity. It should be understood that a typical environment may include more or fewer devices than illustrated in FIG. 1. For example, BP monitor 120 is shown as a separate element from the other devices. In other implementations, BP monitor 120 and/or other devices (e.g., hemoglobin monitor 130) may be part of monitoring device 140. In addition, in some implementations, the functions described below as being performed by multiple devices in environment 100 may be performed by a single device. For example, in some implementations, the functions performed by hemoglobin monitor 130 and monitoring device 140 may be combined into a single device. In addition, in an alternative implementation, some elements may not be used.

Figure 2:
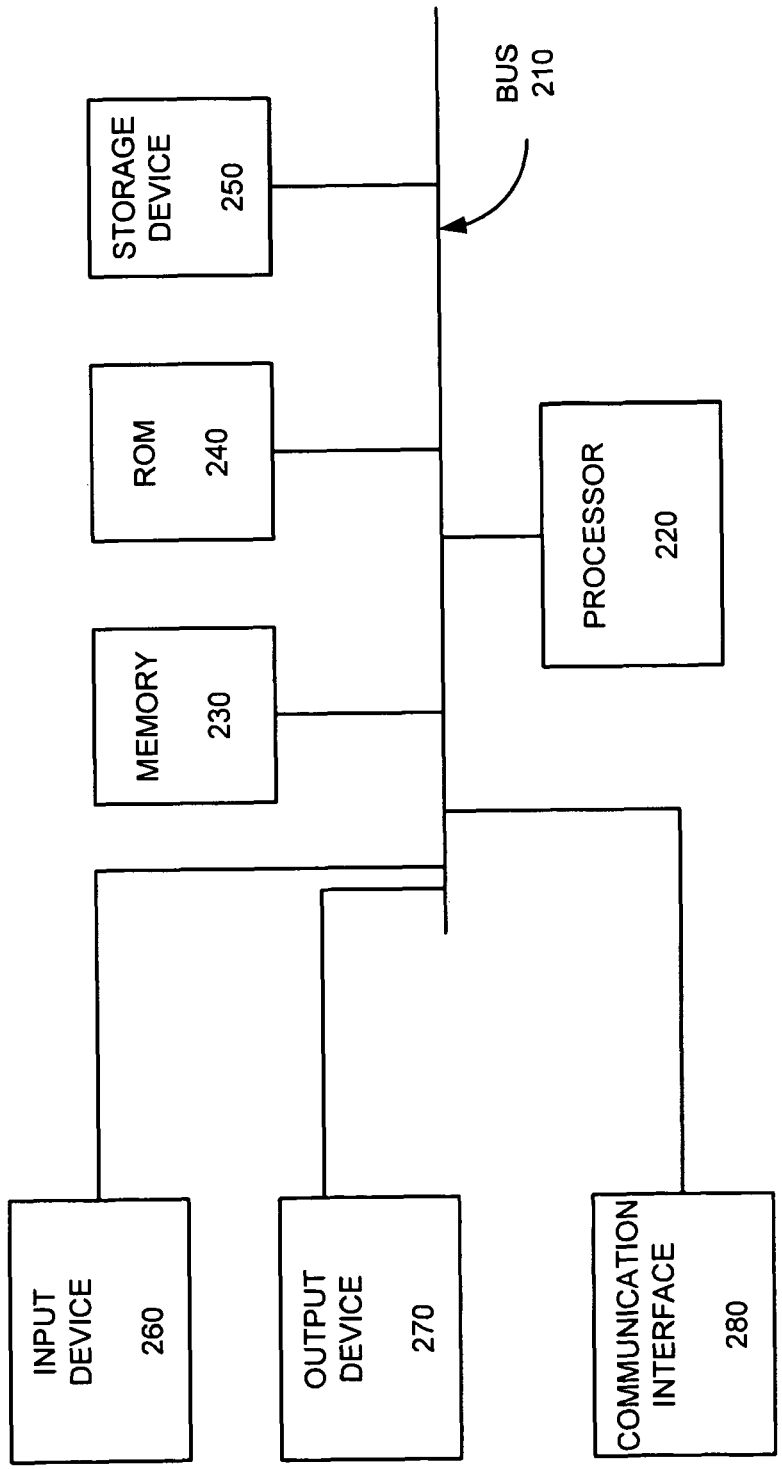
FIG. 2 illustrates an exemplary configuration of the monitoring device of FIG. 1.

FIG. 2 illustrates an exemplary configuration of monitoring device 140. Referring to FIG. 2, monitoring device 140 may include a bus 210, a processor 220, a main memory 230, a read only memory (ROM) 240, a storage device 250, an input device 260, an output device 270, and a communication interface 280. Bus 210 may include a path that permits communication among the elements of monitoring device 140.

Processor 220 may include one or more processors, microprocessors, application specific integrated circuits (ASICs), field programmable gate arrays (FPGAs) or processing logic that may interpret and execute instructions. Memory 230 may include a random access memory (RAM) or another type of dynamic storage device that may store information and instructions for execution by processor 220. ROM 240 may include a ROM device or another type of static storage device that may store static information and instructions for use by processor 220. Storage device 250 may include a magnetic and/or optical recording medium and its corresponding drive.

Input device 260 may include a mechanism that permits an operator to input information to monitoring device 140, such as a keyboard, a mouse, a pen, voice recognition and/or biometric mechanisms, etc. Output device 270 may include a mechanism that outputs information to the operator, including a display, a printer, a speaker, etc. Communication interface 280 may include any transceiver-like mechanism that enables monitoring device 140 to communicate with other devices and/or systems. For example, communication interface 280 may include an interface for communicating with (e.g., receiving data from) BP monitor 120 and hemoglobin monitor 130. Communication interface 280 may also include a modem or an Ethernet interface to a LAN. Alternatively, communication interface 280 may include other mechanisms for communicating via a network (not shown).

Monitoring device 140 may perform processing associated with monitoring patient 110, as described in detail below. According to an exemplary implementation, monitoring device 140 may perform these operations in response to processor 220 executing sequences of instructions contained in a computer-readable medium, such as memory 230. A computer-readable medium may be defined as a physical or logical memory device.

The software instructions may be read into memory 230 from another computer-readable medium, such as data storage device 250, or from another device via communication interface 280. The software instructions contained in memory 230 may cause processor 220 to perform processes that will be described later. Alternatively, hard-wired circuitry may be used in place of or in combination with software instructions to implement processes described herein. Thus, implementations described herein are not limited to any specific combination of hardware circuitry and software.

Figure 3:
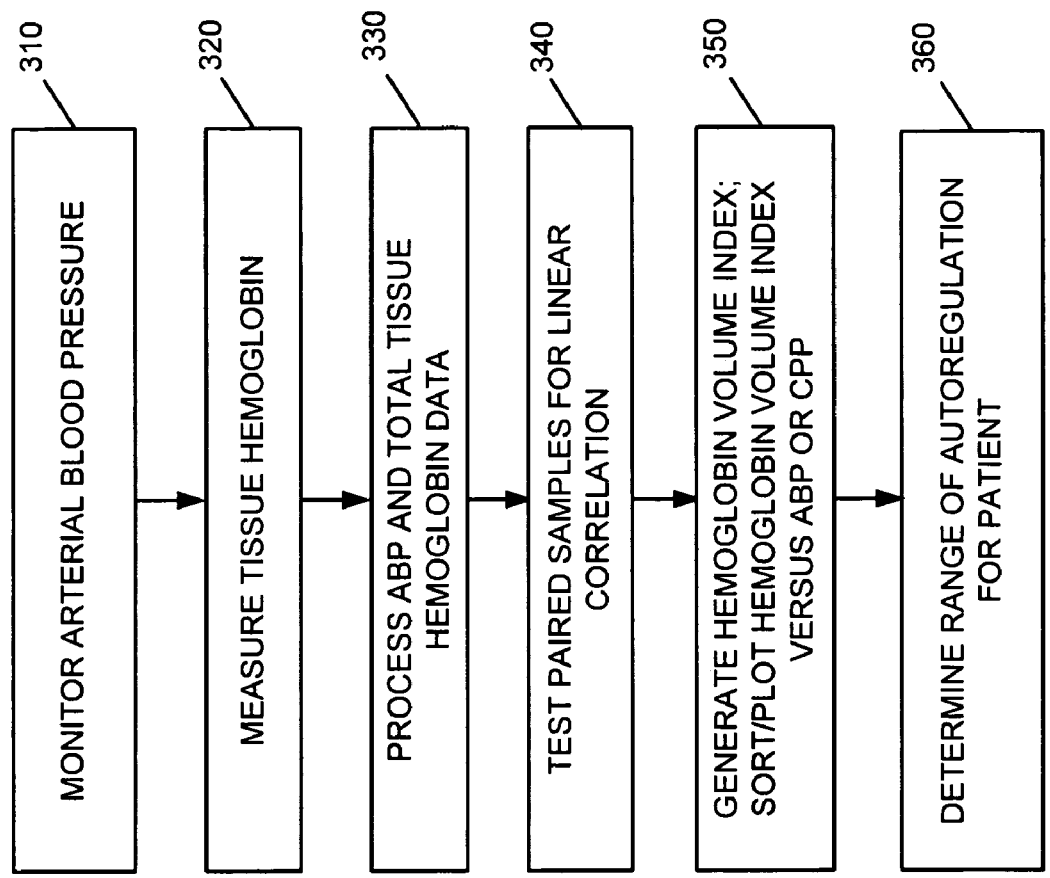
FIG. 3 is a flow diagram illustrating exemplary processing by various devices illustrated in FIG. 1.

FIG. 3 is a flow diagram illustrating exemplary processing associated with monitoring patient 110. In this example, assume that patient 110 is experiencing some type of medical distress. BP monitor 120 maybe used to measure the ABP of patient 110 (act 310). For example, as discussed above, a catheter (not shown in FIG. 1) may be inserted into an artery of patient 110 to measure ABP in a continuous manner. In alternative implementations, a non-invasive BP monitoring device, such as a monitoring device that uses a finger cuff placed on a finger of patient 110, may be used to monitor ABP of patient 110, instead of using a catheter.

In an exemplary implementation, BP monitor 120 may sample the ABP of patient 110 at a frequency ranging from, for example, 60-100 times per second (e.g., 60-100 Hertz (Hz)). Other frequencies of monitoring (e.g., lower than 60 Hz or higher than 100 Hz), may be used in alternative implementations. The sampled ABP data may be provided to monitoring device 140, as described in more detail below.

Hemoglobin monitor 130 may also be coupled to patient 110 and measure the total tissue hemoglobin in the brain of patient 110 (act 320). For example, in one implementation, hemoglobin monitor 130 may include a near IR spectroscopy device that is connected to the skull of patient 110 and outputs near IR radiation into the skull of patient 110. Hemoglobin monitor 130 may also include a detector connected to the skull of patient 110 that detects absorption of the near IR radiation within the brain. Based on the amount of absorption of the near IR radiation and/or the absorption spectra at various frequencies by brain tissue, hemoglobin monitor 130 may determine an amount of relative total tissue hemoglobin in the brain (e.g., rTHb), or region of the brain that is being monitored. In an exemplary implementation, hemoglobin monitor 130 may measure the rTHb in the brain of patient 110 in this manner every predetermined period of time, such as every two seconds. Other periods for measuring the rTHb may be used in alternative implementations.

As illustrated in FIG. 1, BP monitor 120 and hemoglobin monitor 130 may be coupled to monitoring device 140. BP monitor 120 and hemoglobin monitor 130 may output the ABP measurements and hemoglobin measurements, respectively, to monitoring device 140. Communication interface 280 (FIG. 2) may receive the outputted data. In an exemplary implementation, processor 220 (FIG. 2) may receive the data values corresponding to the ABP and total tissue hemoglobin in a continuous, real-time or near real-time manner as they are generated by BP monitor 120 and hemoglobin monitor 130.

Processor 220 may process both the ABP data and the total tissue hemoglobin data (act 330). For example, processor 220 may time integrate the data/samples from BP monitor 120 and hemoglobin monitor 130 every predetermined period of time, such as every 10 seconds. Sampling the ABP and hemoglobin data in this manner essentially generates a 10 second moving average filter for the ABP and total tissue hemoglobin data. Other sampling periods may be used in alternative implementations.

Processor 220 may cache the calculated means or averages for both data sets in memory, such as memory 230. Processor 220 may also test paired samples of the two data sets (i.e., the ABP data and the total tissue hemoglobin data) for linear correlation (act 340). Testing paired samples of the two data sets essentially corresponds to testing samples of a continuous ABP waveform and a continuous total tissue hemoglobin waveform. In an exemplary implementation, monitoring device 140 may pair synchronously obtained samples (e.g., samples associated with the same period of time) of the ABP and total tissue hemoglobin data and test for linear correlation using a Pearson coefficient.

For example, for a series of n measurements of variables X and Y written as $x_i$ and $y_i$, where i=1, 2, . . . , n, the Pearson correlation coefficient, also referred to as the Pearson product-moment correlation coefficient, can be used to estimate the correlation between X and Y. The Pearson coefficient, $r_{xy}$, may be expressed as:

$$r_{xy} = \frac{\sum x_i y_i - n\overline{x}\overline{y}}{(n-1)s_x s_y}$$

$$= \frac{n\sum x_i y_i - \sum x_i \sum y_i}{\sqrt{n\sum x_i^2 - (\sum x_i)^2} \sqrt{n\sum y_i^2 - (\sum y_i)^2}}$$

$$r_{xy} = \frac{\sum (x_i - \overline{x})(y_i - \overline{y})}{(n-1)s_x s_y},$$

where $\overline{x}$ and $\overline{y}$ are the sample means of X and Y, $s_x$ and $s_y$ are the sample standard deviations of X and Y and the sum is from i=1 to n. In this example, X may correspond to ABP measurements and Y may correspond to total tissue hemoglobin measurements (e.g., rTHb). The Pearson coefficients range from 1 to −1, where the closer the coefficient is to 1 or −1, the stronger the correlation between the variables. A correlation of 1 indicates an increasing linear relationship and a correlation of −1 indicates a decreasing linear relationship.

In an exemplary implementation, processor 220 may test 30 paired samples of the mean ABP and the mean total tissue hemoglobin for analysis. In the example above, in which sampling occurs every 10 seconds, the 30 paired samples correlate to 300 seconds worth of data from patient 110. Processor 220 may then output a Pearson coefficient indicating a degree of correlation between the ABP data and total tissue hemoglobin data (act 350). This correlation coefficient may correspond to a hemoglobin volume value or a hemoglobin volume index (HVx).

Processor 220 may generate an HVx value every predetermined period of time, such as at least once every 60 seconds. In this manner, an HVx is generated continuously (e.g., every 60 seconds) in overlapping windows of time that each represent 300 seconds of data from patient 110.

Processor 220 may sort the HVx values based on the average ABP or CPP associated at which they were measured (act 350). For example, in one implementation, processor 220 may generate a plot of HVx values as a function of the corresponding ABP or CPP at which the HVx values were generated and output the plot for viewing via output device 270 (act 350). The corresponding plot may then be used to determine a range of autoregulation for patient 110 (act 360).

For example, the HVx may show a relatively high correlation to cerebral vascular reactivity to allow medical personnel to determine when the autoregulatory functions of the brain are within an acceptable range. In animal subjects, such as piglets, values of HVx below zero have been shown to be indicative of intact vascular reactivity, and values of HVx above 0.2 have been shown to be indicative of impaired vascular reactivity. Medical personnel may then determine the ABP or CPP at which autoregulation begins to fail and attempt to set the ABP or CPP of patient 110 such that the autoregulatory mechanism of the brain will function. In this manner, generating a hemoglobin volume index and plotting this value against ABP or CPP enables medical personnel to attempt to use medication or other intervention means to maintain patient 110's CPP and/or ABP at the appropriate levels. In some instances, the HVx values may be used to augment other methods of assessing cerebral vascular reactivity, as described in more detail below.

For illustrative purposes, FIGS. 4A-9B illustrate results of an experiment involving an animal subject (i.e., a piglet) that shows how a hemoglobin volume index may be used as a proxy for assessing cerebral autoregulation. Similar results would be expected for human subjects.

Referring to FIG. 4A, an ABP waveform 410 of a piglet with progressive hypotension is shown over a period of time. The units on the y-axis in FIG. 4A are millimeters of mercury. As illustrated, waveform 410 shows that the ABP varies over time and begins to fluctuate at time T and decrease significantly thereafter. FIG. 4A also illustrates cerebral perfusion pressure (CPP) waveform 420 and intra-cranial pressure (ICP) waveform 430 for the piglet. CPP, as discussed above, is defined as the net pressure to the brain. For example, CPP may be defined as the ABP minus the ICP. As illustrated, as ICP rises, the difference between ABP waveform 410 and CPP waveform 420 increases. As ABP falls, vessel reactivity is reflected in the ICP and total hemoglobin measurements, as described in more detail below.

FIG. 4B illustrates the ICP waveform 430 in more detail and FIG. 4C illustrates an rTHb waveform 440 for the piglet in arbitrary units during the monitored period. The rTHb waveform 440 corresponds to the total tissue hemoglobin values generated by hemoglobin monitor 130 described above. As illustrated by the dotted lines connecting various peaks in ICP waveform 430 with peaks in rTHb waveform 440, waveforms 430 and 440 correlate. That is, the peaks in waveforms 430 and 440 are "in phase." This correlation supports the finding that vessel reactivity would produce similar slow wave changes in both measurements (i.e., ICP and total hemoglobin).

Autoregulation may also be measured continuously using slow waveform analysis of laser-Doppler red blood cell flux in the brain and percent oxygen saturation for blood in the brain. For example, referring to FIG. 5A, ABP waveform 410, CPP waveform 420 and ICP waveform 430 are illustrated. FIG. 5B illustrates a laser-Doppler flux waveform 510 measured in arbitrary units and FIG. 5C illustrates a percent oxygen saturation waveform 520 measured in arbitrary units. As illustrated, laser-Doppler red blood cell flux and oxygen saturation in the blood are in phase with one another. That is, waveforms 510 and 520 show a relatively high degree of correlation.

FIG. 6A illustrates ABP waveform 410, CPP waveform 420 and ICP waveform 430. FIG. 6B illustrates a laser-Doppler red blood cell flux-derived index of autoregulation (LDx) 610 and a cerebral oximetry-derived index of autoregulation (COx) 620. As illustrated, waveforms 610 and 620 are closely correlated with each other. FIG. 6C illustrates a pressure reactivity index (PRx) waveform 630 and a hemoglobin volume index (HVx) waveform 640. HVx waveform 640 corresponds to the HVx values generated by monitoring device 140 and plotted via a continuous waveform. In some conventional methods used to assess vascular reactivity, PRx values have been used. Such methods have shown good correlation between PRx and vascular reactivity. For example, when PRx values are negative or zero, vascular reactivity has been shown to remain intact. However, when PRx values are greater than 0.2, vascular reactivity has been shown to be no longer intact and as a result, autoregulation is severely diminished. As illustrated, PRx waveform 630 and HVx waveform 640 are in phase and closely correlate with one another. Therefore, HVx values generated in the manner described above would also be expected to provide good correlation to vascular reactivity. In some implementations, HVx values may be used to augment or supplement PRx values or other measures of vascular reactivity.

FIGS. 6A-6C also illustrate that vessel reactivity may remain intact when autoregulation has been lost. For example, the area inside the dotted oval in FIGS. 6A-6C may represent areas in which autoregulation has been lost, but vessel reactivity is still working. This could occur, as shown in the example provided, when vascular reactivity is still operable, but is overwhelmed by large swings in arterial blood pressure. In this circumstance, a measure of vascular reactivity shows intact readings, but a measure of autoregulation indicates impairment.

FIG. 7A illustrates ABP waveform 410, CPP waveform 420 and ICP waveform 430. FIGS. 7B and 7C illustrate PRx and HVx, respectively, plotted against CPP. As illustrated in FIG. 7B, the pressure reactivity value (i.e., PRx) is zero or negative at a CPP of greater than about 35 mm of mercury. Such a PRx value has been shown to indicate intact vessel reactivity. Similarly, in FIG. 7C, the hemoglobin volume index (i.e., HVx) is zero or negative at a CPP of greater than about 35 mm of mercury and positive at CPP values of less than 35 mm of mercury. This may indicate that vascular reactivity, the mechanism of autoregulation, may be lost at a CPP of less than about 35 mm of Hg.

FIG. 8A illustrates ABP waveform 410, CPP waveform 420 and ICP waveform 430. FIG. 8B illustrates a laser-Doppler red blood cell flux plot and FIG. 8C illustrates a cerebral oximetry plot versus CPP. As illustrated, LDx and COx are relatively high at CPP values of less than about 45-50 mm of mercury. This may illustrate that autoregulation is lost when CPP falls below about 50 mm of mercury. Autoregulation measured in this manner can be frame shifted to the right when CPP is the abscissa since autoregulation can fail at a higher pressure than the failure of vessel reactivity.

FIG. 9A illustrates ABP waveform 410, CPP waveform 420 and ICP waveform 430. FIG. 9B illustrates a scatter plot of laser-Doppler red blood cell flux versus CPP. The slope of a best fit line 910 connecting the points having a CPP of less than about 40 mm is fairly steep. In contrast, the slope of a best fit line 920 connecting points having a CPP of greater than 40 mm is essentially flat. The intersection of these lines (e.g., at about 40 mm of mercury) may define an inflection point at which autoregulation begins to fail (e.g., a CPP of less than about 40 mm of mercury)

As described above, FIGS. 4A-9B illustrate an experiment involving a piglet in which HVx is shown to closely mirror PRx. Similar results in humans subjects would be expected. Therefore, HVx would be expected to provide a good assessment for cerebral vascular reactivity.

CONCLUSION

Implementations described herein provide for assessing cerebral vascular reactivity in a continuous manner. Advantageously, the monitoring may be performed in a minimally invasive or non-invasive manner, thereby allowing the monitoring to be performed in virtually any patient, regardless of age and/or condition.

The foregoing description of exemplary implementations provides illustration and description, but is not intended to be exhaustive or to limit the invention to the precise form disclosed. Modifications and variations are possible in light of the above teachings or may be acquired from practice of the invention.

For example, various features have been described above with respect to monitoring device 140 receiving data from hemoglobin monitor 130 that indicates or represents the total tissue hemoglobin (e.g., rTHb concentration) in the brain, or region of the brain. In other implementations, other measures of total hemoglobin in the brain may be used. For example, hemoglobin monitor 130 may measure an absolute or relative total hemoglobin density, volume, concentration, or some other measure representing or associated with the total tissue hemoglobin in the brain. In some instances, hemoglobin monitor 130 may calibrate or normalize the hemoglobin data in some manner. In other instances, the raw data provided by hemoglobin monitor 130 may not be calibrated or normalized and monitoring device 140 may process the data in the manner described above. In each case, monitoring device 140 may receive data from hemoglobin monitor 130 that indicates or represents the total amount, volume, concentration or some other measure of total hemoglobin in the brain. In addition, in each case, the data received form hemoglobin monitor 130 may acts as a surrogate or indicator of cerebral blood volume. Monitoring device 140 may then use the received hemoglobin data to generate a hemoglobin volume index that may be used to assess cerebral vascular reactivity.

In addition various features have been described above with respect to monitoring device 140 continuously generating various values over predetermined periods of time. It should be understood that other monitoring periods may be used. In addition, aspects of the invention have been mainly described above with respect to monitoring vascular reactivity of the brain using a Pearson coefficient. In other implementations, other linear correlation methods may be used. In addition, the processing described above with respect to the brain may be performed on other organs to obtain useful information.

Further, while series of acts have been described with respect to FIG. 3, the order of the acts may be varied in other implementations. Moreover, non-dependent acts may be implemented in parallel.

It will be apparent to one of ordinary skill in the art that various features described above may be implemented in many different forms of software, firmware, and hardware in the implementations illustrated in the figures. The actual software code or specialized control hardware used to implement the various features is not limiting of the invention. Thus, the operation and behavior of the features of the invention were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as a processor, a microprocessor, an application specific integrated circuit, or a field programmable gate array, software, or a combination of hardware and software.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method, comprising:

receiving, by a processing device, arterial blood pressure data associated with a patient;

receiving, by the processing device, tissue hemoglobin data associated with the patient;

calculating, by the processing device, a mean value for the arterial blood pressure data every first period of time;

calculating, by the processing device, a mean value for the tissue hemoglobin data every first period of time; and calculating, by the processing device, a linear correlation between the mean value of the arterial blood pressure data and the mean value for the tissue hemoglobin data.

2. The method of claim 1, wherein the calculating a linear correlation comprises:
   comparing a predetermined number of the mean values of the arterial blood pressure data and the tissue hemoglobin data, and
   generating a hemoglobin volume value every second period of time.

3. The method of claim 2, further comprising:
   outputting, by the processing device, a plurality of linear correlation values, the plurality of linear correlation values corresponding to a continuous hemoglobin volume index.

4. The method of claim 2, further comprising:
   plotting, by the processing device, the hemoglobin volume values against arterial blood pressure or a cerebral perfusion pressure associated with the patient.

5. The method of claim 4, further comprising:
   determining, by the processing device based on the plotting, a range of at least one of arterial blood pressure or cerebral perfusion pressure at which autoregulation for the patient is functioning properly.

6. The method of claim 2, wherein the calculating a linear correlation comprises calculating a Pearson coefficient.

7. The method of claim 6, wherein the calculating a Pearson coefficient comprises comparing paired samples of the arterial blood pressure and the tissue hemoglobin data taken over overlapping periods of time and repeating the comparing at least once every 60 seconds to generate a linear correlation coefficient at least once every 60 seconds.

8. The method of claim 1, further comprising:
   comparing, by the processing device, the linear correlation to a pressure reactivity value; and
   determining, by the processing device, a range of at least one of arterial blood pressure or cerebral perfusion pressure for the patient based on a result of the comparing.

9. A monitoring device, comprising:
   a processor configured to:
     receive arterial blood pressure data associated with a patient,
     receive tissue hemoglobin data associated with the patient, and
     calculate a linear correlation between mean values of the arterial blood pressure data and mean values of the tissue hemoglobin data.

10. The monitoring device of claim 9, wherein the processor is further configured to calculate a linear correlation value every first period of time, and wherein a plurality of linear correlation values comprise an index that corresponds to a hemoglobin volume index of the patient over a period of time.

11. The monitoring device of claim 10, wherein the processor is further configured to:
    determine a range of at least one of arterial blood pressure or cerebral perfusion pressure for the patient based on the linear correlation values.

12. The monitoring device of claim 9, wherein the processor is further configured to:
    calculate the linear correlation every predetermined period of time, and
    associate each linear correlation value to at least one of the arterial blood pressure or a cerebral perfusion pressure of the patient.

13. The monitoring device of claim 12, wherein the processor is further configured to:
    generate a graphical representation of the linear correlation values as a function of the arterial blood pressure or the cerebral perfusion pressure, the monitoring device further comprising:
    an output device configured to display the graphical representation.

14. The monitoring device of claim 9, wherein when calculating a linear correlation, the processor is configured to calculate a Pearson coefficient.

15. The monitoring device of claim 14, wherein when calculating a Pearson coefficient, the processor is configured to compare paired samples of the arterial blood pressure and the tissue hemoglobin data taken over approximately a five minute period of time.

16. The monitoring device of claim 15, wherein the processor is further configured to calculate a Pearson coefficient at least once per minute, wherein the Pearson coefficients correspond to data taken during overlapping five minute periods of time.

17. A computer-readable medium having stored thereon sequences of instructions which, when executed by at least one processor, cause the at least one processor to:
    receive arterial blood pressure data associated with a patient;
    receive tissue hemoglobin data associated with the patient; and
    calculate a linear correlation between mean values of the arterial blood pressure data and mean values of the tissue hemoglobin data.

18. The computer-readable medium of claim 17, wherein when calculating a linear correlation, the instructions cause the at least one processor to calculate a Pearson coefficient.

19. The computer-readable medium of claim 18, wherein when calculating a Pearson coefficient, the instructions cause the at least one processor to:
    compare approximately 30 paired samples of the arterial blood pressure and the tissue hemoglobin data taken over a five minute period.

20. The computer-readable medium of claim 17, further comprising instructions for causing the at least one processor to:
    generate a graphical representation of linear correlation values as a function of the arterial blood pressure or cerebral perfusion pressure of the patient; and
    output the graphical representation to a display device.

21. A system, comprising:
    means for receiving arterial blood pressure data associated with a patient;
    means for receiving hemoglobin data associated with the patient;
    means for calculating a mean value for the arterial blood pressure data every first period of time;
    means for calculating a mean value for the hemoglobin data every first period of time; and
    means for calculating a linear correlation between the mean value of the arterial blood pressure data and the mean value for the hemoglobin data.

* * * * *